(12) United States Patent
Evans et al.

(10) Patent No.: US 11,911,198 B2
(45) Date of Patent: Feb. 27, 2024

(54) X-RAY IMAGING APPARATUS

(71) Applicant: ADAPTIX LTD, Begbroke (GB)

(72) Inventors: Mark Evans, Oxford (GB); Conrad Dirckx, Oxford (GB)

(73) Assignee: ADAPTIX LTD, Begbroke (GB)

( * ) Notice: Subject to any disclaimer, the term of this patent is extended or adjusted under 35 U.S.C. 154(b) by 297 days.

(21) Appl. No.: 17/472,660

(22) Filed: Sep. 12, 2021

(65) Prior Publication Data

US 2022/0008026 A1 Jan. 13, 2022

Related U.S. Application Data

(63) Continuation of application No. PCT/GB2020/050412, filed on Feb. 21, 2020.

(30) Foreign Application Priority Data

Mar. 13, 2019 (GB) ..................................... 1903418

(51) Int. Cl.
  *A61B 6/00* (2006.01)
  *A61B 6/02* (2006.01)
  *A61B 6/14* (2006.01)

(52) U.S. Cl.
  CPC ............ *A61B 6/4007* (2013.01); *A61B 6/025* (2013.01); *A61B 6/145* (2013.01); *A61B 6/4452* (2013.01); *A61B 6/4458* (2013.01)

(58) Field of Classification Search
  CPC .... A61B 6/00; A61B 6/02; A61B 6/14; A61B 6/4007; A61B 6/025; A61B 6/145;

(Continued)

(56) References Cited

U.S. PATENT DOCUMENTS 7,167,541 B2 1/2007 Kaito
2012/0195403 A1 8/2012 Vedantham et al.
(Continued)

FOREIGN PATENT DOCUMENTS

EP 3064140 10/2019
JP 3028330 9/1996
(Continued)

OTHER PUBLICATIONS

UK IPO, Search Report in corresponding GB application 1903418.0, dated Sep. 12, 2019.
(Continued)

*Primary Examiner* — Jurie Yun
(74) *Attorney, Agent, or Firm* — Ryan Alley IP

(57) ABSTRACT

An x-ray imaging apparatus 10 comprising a support structure 100, the support structure supporting two separate x-ray emitting apparatus, a first x-ray emitting apparatus 130 comprising an x-ray emitter arranged for producing 2D tomosynthesis images, and a second x-ray emitting apparatus 140 comprising an array of distributed x-ray emitters arranged for producing 3D tomosynthesis images, the first and second x-ray emitting apparatus moveable relative to the support structure and arranged such that, in use, one of the first and second x-ray emitting apparatus is moveable into an operative position whereby x-rays are emitted therefrom towards a target 200, and simultaneously the other of the first and second x-ray emitting apparatus is movable into an inoperative position whereby x-rays are not emitted therefrom.

19 Claims, 3 Drawing Sheets

(58) Field of Classification Search
CPC ... A61B 6/4458; A61B 6/4452; A61B 6/4429; A61B 6/447
See application file for complete search history.

(56) References Cited

U.S. PATENT DOCUMENTS

| | | |
|---|---|---|
| 2013/0034201 A1 | 2/2013 | Boese et al. |
| 2014/0369459 A1 | 12/2014 | Foos et al. |
| 2015/0036799 A1 | 2/2015 | Zhang et al. |
| 2016/0256128 A1 | 9/2016 | Wang et al. |
| 2018/0055463 A1 | 3/2018 | Fuh et al. |
| 2022/0133249 A1* | 5/2022 | Turner .................. A61B 6/4007 378/38 |

FOREIGN PATENT DOCUMENTS

| | | |
|---|---|---|
| JP | 2005-270201 | 10/2005 |
| JP | 2015-508011 | 3/2015 |
| JP | 2019-195520 | 11/2019 |
| WO | 2006/109808 | 10/2006 |
| WO | 2017/196413 | 11/2017 |
| WO | 2018/073554 | 4/2018 |

OTHER PUBLICATIONS

WIPO, International Search Report and Written Opinion in corresponding PCT application PCT/GB2020/050412, dated Apr. 5, 2020.
JPO, Notice of Reasons for Refusal in corresponding JP application 2021-553080, dated Nov. 1, 2023.

* cited by examiner

X-RAY IMAGING APPARATUS

RELATED APPLICATIONS

This application claims priority under 35 U.S.C. § 120 to, and is a continuation of, co-pending International Application PCT/GB2020/050412, filed Feb. 21, 2020 and designating the US, which claims priority to GB Application 1903418.0, filed Mar. 13, 2019 such GB Application also being claimed priority to under 35 U.S.C. § 119. These GB and International applications are incorporated by reference herein in their entireties.

FIELD

The present invention relates generally to an x-ray imaging apparatus and a method of obtaining 3D tomosynthesis x-ray images of a target and finds particular, although not exclusive, utility in dental x-ray imaging.

BACKGROUND

Conventional 2D dental x-ray imaging devices have existed for many years and they are the world's most prevalent medical x-ray device with an estimated 500 million dental x-ray examinations carried out annually. These devices rely on a single x-ray tube which capture single images in <0.2 sec if combined with a digital intra-oral sensor.

Current 3D systems in dental use are typically Cone Beam Computed Tomography (CBCT), which are expensive (typically US$40,000-US$125,000). They are also bulky (so incapable of fitting in to a typical treatment room), heavy (so incapable of being moved around a dental practice) and give a high dose of X-rays (so requiring shielding in the room in which it is deployed). As a result, CBCT cannot be used inter-operatively. In addition, the acquisition takes several seconds and requires the subject to be stationery (which is difficult to use for some patients such as young children).

Recently, tomosynthesis systems for use in dental imaging have been developed which rely on having an array of low-powered x-ray sources (50-100 uA) within the device. These devices can take several seconds to capture a range of 2D images from the separate sources which are then used to generate 3D images through the use of tomosynthesis reconstruction algorithms. These relatively low-powered arrays of x-ray sources allow for multiple projection images to be acquired in-order to generate high quality tomosynthesis images with good depth resolution at low-dose.

In order to offer clinicians an initial review image, it is possible to create a 'synthetic 2D' image by re-processing the stack of 2D images created by the 3D reconstruction. However, the limitation of these low-powered sources is that it is not possible to acquire a single projection image with the same contrast-to-noise ratio in the same time as a conventional 2D system. Also, the stand-off distance required for a conventional 2D image is often different from that required for a 3D image such that trying to create a synthetic 2D image from a 3D image can cause magnification effects distorting the image. Therefore, if both types of imaging are desirable it is necessary to have two separate systems in the same examination room. This has the disadvantage of greater cost, space and the need to reposition the patient between examinations.

SUMMARY

In a first aspect, the invention provides an x-ray imaging apparatus comprising a support structure, the support structure supporting two separate x-ray emitting apparatus, a first x-ray emitting apparatus comprising an x-ray emitter arranged for producing 2D images, and a second x-ray emitting apparatus comprising an array of distributed x-ray emitters arranged for producing 3D tomosynthesis images, the first and second x-ray emitting apparatus moveable relative to the support structure and arranged such that, in use, one of the first and second x-ray emitting apparatus is moveable into an operative position whereby x-rays are emitted therefrom towards a target, and simultaneously the other of the first and second x-ray emitting apparatus is movable into an inoperative position whereby x-rays are not emitted therefrom.

The first x-ray emitting apparatus may comprise a single-source x-ray emitter.

The second x-ray emitting apparatus may comprise a Flat Panel x-ray Source (FPS).

In this way, only one x-ray imaging apparatus is required but two different forms of x-ray imaging are possible. Furthermore, the two different emitting apparatus are arranged on the same support structure with the ability to bring each into operation as required and take out of operation the other one. This avoids both x-ray emitting apparatus operating at the same time to avoid overdosing of the patient and/or accidental exposure to the clinician.

For instance, each of the two x-ray emitting apparatus may be attached to a shaft around which they rotate. It is also contemplated that they may rise and fall up and down this shaft as they are rotated about it, as required, bringing them into the operative position.

Each of the first and second x-ray emitting apparatus may be movable independently of one another relative to the support structure.

The first and second x-ray emitting apparatus may be arranged on the support structure such that the location and direction of a central axis of x-rays emitted from the first x-ray emitting apparatus when in the operative position is approximately identical to the location and direction of a central axis of x-rays emitted from the second x-ray emitting apparatus when in the operative position.

The first and second x-ray emitting apparatus may be arranged on the support structure such that with the first x-ray emitting apparatus in the operative position the stand-off distance between it and the target has a first value, and with the second x-ray emitting apparatus in the operative position the stand-off distance between it and the target has a second value.

The first value may be approximately 20 cm and the second value may be approximately 10 cm. Other dimensions are contemplated.

There may be only one operative position relative to the support structure into which the first and second x-ray emitting apparatus may be brought.

The first and second x-ray emitting apparatus may each comprise at least one collimator. The apparatus may further comprise a mounting to which both the first and second x-ray emitting apparatus are attached such that the angle between the longitudinal bores of the at least one collimator on each of the two x-ray emitting apparatus is approximately 90 degrees.

In this manner, one x-ray emitting apparatus could be aimed at the patient, when in the operative position, and the other x-ray emitting apparatus aimed at the ceiling or floor, when in the inoperative position. This may ensure that the clinician is not irradiated accidentally.

The first and second x-ray emitting apparatus may each comprise at least one collimator. The apparatus may further comprise a mounting to which both the first and second x-ray emitting apparatus are attached such that the angle between the longitudinal bores of the at least one collimator on each of the two x-ray emitting apparatus is approximately 180 degrees.

In this manner, one x-ray emitting apparatus could be aimed at the patient and the other x-ray emitting apparatus aimed at a wall. This may ensure that the clinician is not irradiated accidentally.

Other angles between the longitudinal bores of the at least one collimator on each of the two x-ray emitting apparatus are contemplated, such as 50 degrees, 135 degrees etc.

The mounting may be arranged on the support structure such that with the first x-ray emitting apparatus in the operative position the location and direction of a central axis of x-rays emitted from the first x-ray emitting apparatus is approximately identical to the location and direction of a central axis of x-rays emitted from the second x-ray emitting apparatus with the second x-ray emitting apparatus in the operative position.

In this regard, the term central axis may be understood as an axis extending orthogonally away from an approximate centre of the emitter(s) in the general direction of the x-ray emission path defining a mean direction.

This might be useful, for instance, in the situation where the support structure is arranged on the end of a movable arm. The arm may be moved from a stowed position until a first of the two x-ray emitting apparatus is located correctly for use with a patient and in the operative position. If it is then desirable to use the second x-ray emitting apparatus, the first and second x-ray emitting apparatus may be moved relative to the support structure to bring the second x-ray emitting apparatus into the operative position and aim it at the patient, and simultaneously move the first x-ray emitting apparatus into the inoperative position aimed away from the patient.

Weights may be arranged on the support structure to aid with the balance of the x-ray imaging apparatus.

Using the example above, this additional feature enables the support structure to remain stationary relative to the patient meaning that the patient need not be disturbed when changing from an operative first or second x-ray emitting apparatus to the other of the first or second x-ray emitting apparatus.

The mounting may be arranged on the support structure such that with the first x-ray emitting apparatus in the operative position the stand-off distance between it and the target has a first value, and with the second x-ray emitting apparatus in the operative position the stand-off distance between it and the target has a second value.

This allows for different stand-off distances which may be required by the two different x-ray emitting apparatus for optimum operation. Again, having this feature enables the support structure to remain stationary with either of the first or second x-ray emitting apparatus in the operative position. In other words, the clinician would not have to pull the x-ray emitting apparatus away from the patient, or push it towards them, simply because the first x-ray emitting apparatus has been exchanged for the second.

The first value may be approximately 20 cm and the second value may be approximately 10 cm. Other dimensions are contemplated.

The x-ray imaging apparatus may further include at least one interlock which enables whichever of the first and second x-ray emitting apparatus is in the operative position to emit x-rays. In this manner, only when one of the x-ray emitting apparatus is in the correct operative position is it energisable to emit x-rays. This prevents either of the x-ray emitting apparatus from emitting x-rays when in any position other than the operative position. Such interlocks are well known and can comprise solenoids, switches, sensors and the like which can be used to electrically isolate one of the x-ray emitting apparatus from the power supply to avoid accidental discharge, or connect it to the power supply to enable it to operate.

The x-ray imaging apparatus may include a sensor, such as an intra-oral sensor for receiving the x-rays after they have passed through the target. The sensor may be a digital sensor such that images in digital format may be created from the received x-rays for viewing, for example, on a display screen. The sensor may be a Flat Panel x-ray Detector (FPD).

In use, the x-ray source and sensor may work in conjunction along with a processor which acts as an 'Acquisition Workstation' to analyse the output of the FPD and reconstruct multiple frames into a 3D model which can be exported (often via a Picture Archiving and Communication System ('PACS')) to a 'Visualization Workstation' on which a clinician may review the images using viewing software.

The first x-ray emitting apparatus may operate at a current in the range of 2.5 mA to 7 mA, and a voltage in the range of 60 to 70 kV.

The second x-ray emitting apparatus may operate at a current in the range of 1 mA to 3 mA.

The x-ray imaging apparatus may further comprise a common power supply for both first and second x-ray emitting apparatus. Other currents and voltage are contemplated. This may reduce the size, complexity and cost of the x-ray imaging apparatus.

In a second aspect, the invention provides a method of obtaining 3D tomosynthesis x-ray images of a target, comprising the steps of: providing an x-ray imaging apparatus according to the first aspect; providing a target; arranging the first x-ray emitting apparatus in the operative position such that it is aimed at the target; operating the apparatus to provide a 2D x-ray image of the target; moving the first x-ray emitting apparatus into the inoperative position and moving the second x-ray emitting apparatus into the operative position such that it is aimed at the target; operating the apparatus to provide 3D tomosynthesis x-ray images of the target.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

Figure 1:
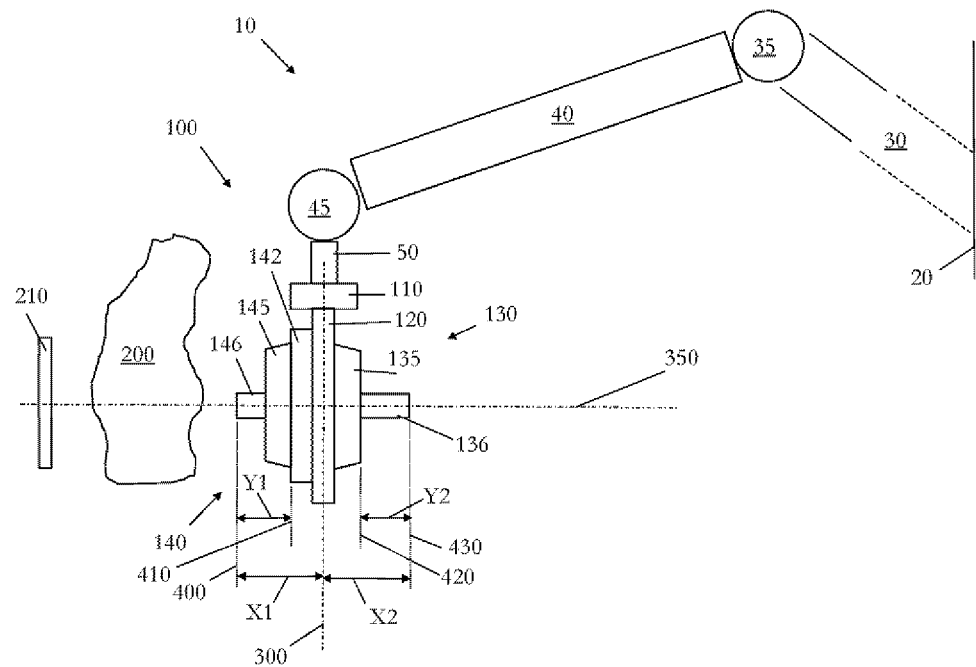
FIG. 1 is a schematic diagram of a first x-ray imaging apparatus.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein. Likewise, method steps described or claimed in a particular sequence may be understood to operate in a different sequence.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any one embodiment or aspect of the invention may be combined in any suitable manner with any other particular feature, structure or characteristic of another embodiment or aspect of the invention, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

In FIG. 1 an x-ray imaging apparatus 10 is shown schematically. The apparatus 10 includes an arm 30, 40 attached to a wall 20. The arm 30, 40 includes joints 35, 45 to enable the free end to be located anywhere within a volume of space distal from the wall. The connection of the arm 30 to the wall 20 may include a joint (not shown).

At the free end of the arm 40 a support structure 100 is arranged comprising a mounting 120 to which are attached a 2D x-ray emitting apparatus 130 on one side, and a 3D x-ray emitting apparatus 140 on the opposite side.

The mounting 120 is attached to the free end of the arm 40 via rotatable joint 110 and a connecting rod 50.

The mounting 120 is rotatable about an axis (indicated by broken line 300) via the rotatable joint 110.

The 2D x-ray emitting apparatus 130 comprises an x-ray emitter 135 and a collimator 136. Likewise, the 3D x-ray emitting apparatus 140 comprises an x-ray emitter array 145 and a collimator 146. However, the x-ray emitter array 145 is arranged away from the mounting 120 via a spacer 142.

The 3D x-ray emitting apparatus 140 is shown in the operative position in that in use x-rays will emerge from the collimator 146, pass through the target 200 and be sensed by the sensor 210 arranged on the other side of the target 200 from the x-ray emitting apparatus 140.

To allow the 2D x-ray emitting apparatus 130 to operate instead of the 3D x-ray emitting apparatus 140, the mounting 120 is rotated about the rotatable joint 110 such that the 2D x-ray emitting apparatus 130 will be on the left-hand side of the mounting 120 as shown in the Figure, and the 3D x-ray emitting apparatus 140 will be on the right-hand side.

The spacer 142 enables the different stand-off distances required for each of the two x-ray emitting apparatus to not require the arm or support structure 100 to have to be moved after changing from the 3D to the 2D x-ray emitting apparatus.

This is shown by the dotted lines 400, 410, 420, 430 in the Figure. The distance between the front of the 3D collimator and the 3D x-ray emitter array is the 3D stand-off distance Y1. The distance between the front of the 2D collimator and the 2D x-ray emitter is the 2D stand-off distance Y2. The distance between the front of the 3D collimator and the pivot axis 300 is indicated as X1. The distance between the front of the 2D collimator and the pivot axis 300 is indicated as X2. Even though Y1 and Y2 are different dimensions, X1 is the same as X2 due to the spacer 142.

Accordingly, the position of the front of the 2D collimator 146 (in the left operative position) relative to the target 200 is the same as the front of the 3D collimator 136 relative to the target (with the 3D x-ray emitting apparatus in the left operative position).

Furthermore, the 2D x-ray emitting apparatus and 3D x-ray emitting apparatus are arranged such that their central axes are co-axial as shown by broken line 350. The rotation axis 300 is arranged orthogonally to the central axis 350 such that with either x-ray emitting apparatus in the operative position the central axes are identical.

Although not shown, the two x-ray emitting apparatus will be connected to a controller. Likewise, the sensor 210 will be connected to a processor and display means such as a screen.

An alternative to using a spacer, to ensure that the different stand-off distances are obtainable from the two x-ray emitting apparatus, is to have the mounting pivoted eccentrically relative to the joint 110.

Figure 2:
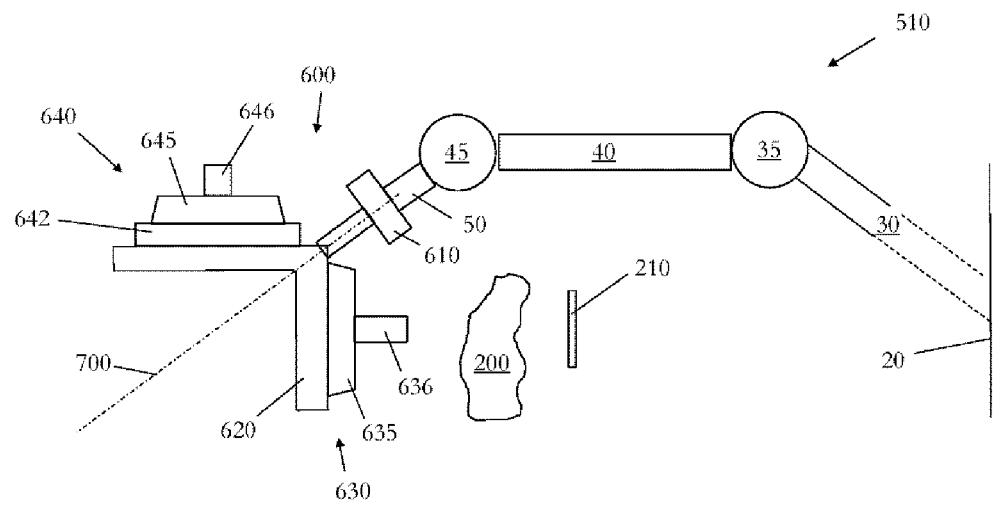
FIG. 2 is a schematic diagram of a second x-ray imaging apparatus in a first position.

In FIG. 2, an alternative x-ray imaging apparatus 510 is schematically shown. It also comprises an arm 30, 40 attached to a wall 20 with articulated joints 35, 45 allowing the free end to be located anywhere within a volume of space distal from the wall. The connection of the arm 30 to the wall 20 may include a joint (not shown).

At the free end of the arm an alternative support structure 600 is shown comprising an L shaped mounting 620. In the Figure, one arm is arranged horizontally and one arm is arranged vertically depending from the right-hand end of the horizontal arm. On the vertical arm a 2D x-ray emitting apparatus 630 is attached, and on the horizontal arm a 3D x-ray emitting apparatus 140 is attached. Both face outwardly away from the inner angle between the two arms.

The mounting 620 is attached to the free end of the arm 40 via rotatable joint 610 and a connecting rod 50.

The mounting 620 is rotatable about an axis (indicated by broken line 700) via the rotatable joint 610. The axis 700 is arranged to lie between the two arms of the mounting 620 such that is at 45 degrees away from each of the two arms.

The 2D x-ray emitting apparatus 630 comprises an x-ray emitter 635 and a collimator 636. Likewise, the 3D x-ray emitting apparatus 640 comprises an x-ray emitter array 645 and a collimator 646. However, the x-ray emitter array 645 is arranged away from the mounting 620 via a spacer 642.

The 2D x-ray emitting apparatus 630 is shown in the operative position in that in use x-rays will emerge from the collimator 636, pass through the target 200 and be sensed by the sensor 210 arranged on the other side of the target 200 from the x-ray emitting apparatus 630.

To allow the 3D x-ray emitting apparatus 640 to operate instead of the 2D x-ray emitting apparatus 630, the mounting 620 is rotated about the rotatable joint 610 such that the arms will exchange places so that the previously horizontal arm which includes the 3D x-ray emitting apparatus 640 will be in a vertical position on the right-hand side of the axis 700 as shown in the Figure, and the previously vertical arm which includes the 2D x-ray emitting apparatus 630 will be in a horizontal position above and to the left of the axis 700 as shown in the Figure.

The spacer 642 enables the different stand-off distances required for each of the two x-ray emitting apparatus to not require the arm or support structure 600 to have to be moved after changing from the 3D to the 2D x-ray emitting apparatus, in a similar manner to that described with regard to FIG. 1.

Figure 3:
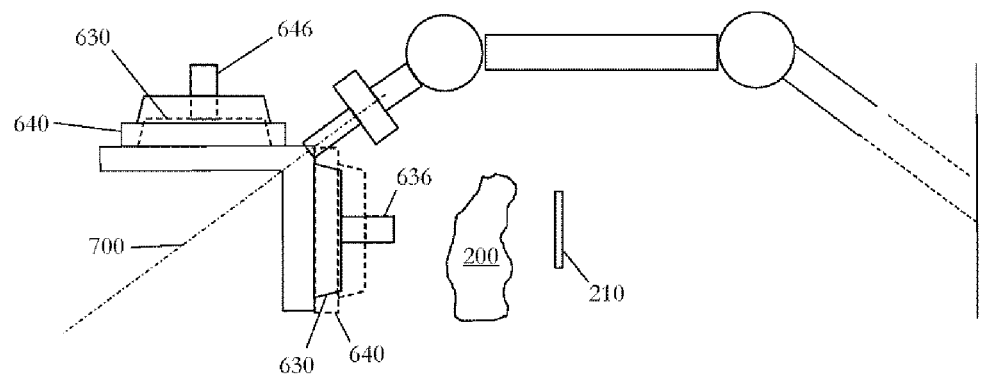
FIG. 3 a schematic diagram of the second x-ray imaging apparatus in a second position.

FIG. 3 shows the same apparatus as FIG. 2 but also includes the 2D x-ray emitting apparatus and 3D x-ray emitting apparatus in exchanged paces, with the support structure 600 having been rotated about the axis 700, in broken lines. It can be seen how the collimators are located in the same places such that the central axes are identical in location and direction.

Figure 4:
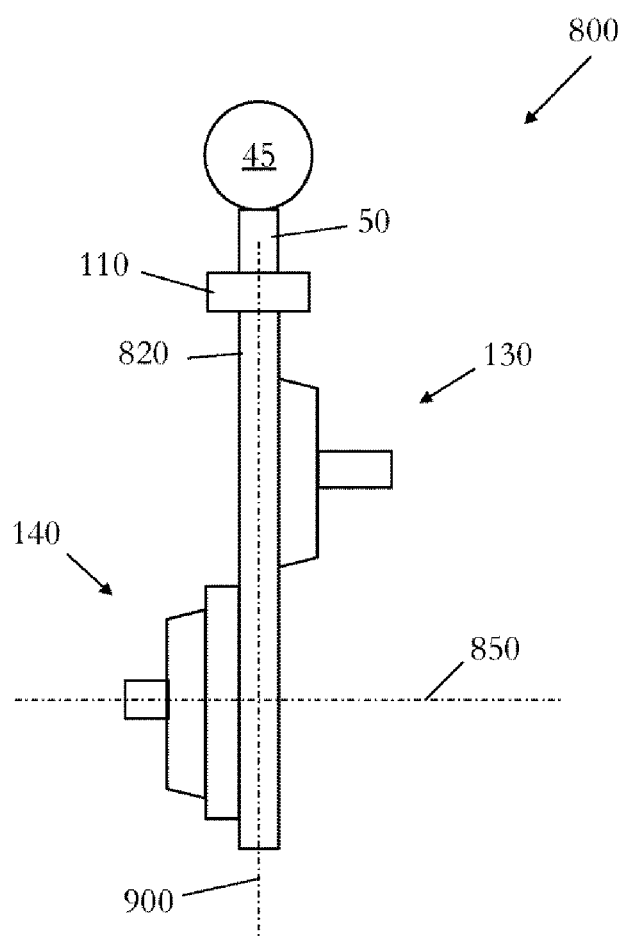
FIG. 4 is a schematic diagram of part of a third x-ray imaging apparatus.

An alternative support structure 800 is shown in FIG. 4. This support structure 800 may be connected to the end of an arm as shown in FIGS. 1 to 3 via a joint 45, connecting rod 50 and rotatable joint 110, although not all of these members are necessarily required, dependent on the type of use.

A mounting 820 in the form of a shaft depends from the joint 45. The two x-ray emitting apparatus 130, 140 are both movably and rotatably attached to the mounting 820. The means of attachment may take the form of pins extending into channels (not shown) provided within the mounting, the pins being slidably captive within the channels.

In the Figure, the second x-ray emitting apparatus 140 is shown in the operative position, which is lowermost on the mounting 820, facing left, with its horizontal central axis 850 as shown by the broken line. By contrast, the first x-ray emitting apparatus 130 is shown in the uppermost inoperative position, facing right.

To bring the first x-ray emitting apparatus 130 into the operative position and simultaneously take the second x-ray emitting apparatus 140 to the inoperative position the two x-ray emitting apparatus may be slidably moved in a partial spiral manner around the mounting 820 via the pins and channels such that the first x-ray emitting apparatus 130 now faces left and the second x-ray emitting apparatus 140 now faces right. As the second x-ray emitting apparatus 140 is moved upwardly in one channel, the first x-ray emitting apparatus 130 may be moved downwardly in another channel. The movement of the x-ray emitting apparatus may be effected by hand or may be motorised.

An alternative possibility is that the channels are arranged substantially vertically, linearly along the mounting and parallel with the longitudinal axis of the shaft. In this way, each x-ray emitting apparatus 130, 140 may occupy the upper inoperative position or the lower operative position. The mounting 820 would need to be rotated 180 degrees around axis 900 relative to the joint 45 to ensure that whichever x-ray emitting apparatus is lowermost faces left, however, the structure may be arranged such that the central axis 850 of whichever x-ray emitting apparatus is lowermost is constant and uniform.

Interlocks may be provided in either arrangement described to ensure that only when an x-ray emitting apparatus is in the operative position can it emit x-rays but when not in the operative position it cannot emit x-rays.

The invention claimed is:

1. An x-ray imaging apparatus comprising a support structure, the support structure supporting two separate x-ray emitting apparatus, a first x-ray emitting apparatus comprising an x-ray emitter arranged for producing 2D images, and a second x-ray emitting apparatus comprising an array of distributed x-ray emitters arranged for producing 3D tomosynthesis images, the first and second x-ray emitting apparatus moveable relative to the support structure and arranged such that, in use, one of the first and second x-ray emitting apparatus is moveable into an operative position whereby x-rays are emitted therefrom towards a target, and simultaneously the other of the first and second x-ray emitting apparatus is movable into an inoperative position whereby x-rays are not emitted therefrom.

2. The x-ray imaging apparatus according to claim 1, wherein each of the first and second x-ray emitting apparatus are movable independently of one another relative to the support structure.

3. The x-ray imaging apparatus according to claim 1, wherein the first and second x-ray emitting apparatus are arranged on the support structure such that the location and direction of a central axis of x-rays emitted from the first x-ray emitting apparatus when in the operative position is approximately identical to the location and direction of a central axis of x-rays emitted from the second x-ray emitting apparatus when in the operative position.

4. The x-ray imaging apparatus according to claim 3, wherein the first and second x-ray emitting apparatus are arranged on the support structure such that with the first x-ray emitting apparatus in the operative position the stand-off distance between it and the target has a first value, and with the second x-ray emitting apparatus in the operative position the stand-off distance between it and the target has a second value.

5. The x-ray imaging apparatus according to claim 4, wherein the first value is approximately 20 cm and the second value is approximately 10 cm.

6. The x-ray imaging apparatus according to claim 1, wherein the first and second x-ray emitting apparatus each comprise at least one collimator, the apparatus further comprising a mounting to which both the first and second x-ray emitting apparatus are attached such that an angle between longitudinal bores of the at least one collimator on each of the two x-ray emitting apparatus is approximately 90 degrees.

7. The x-ray imaging apparatus according to claim 6, wherein the mounting is arranged on the support structure such that with the first x-ray emitting apparatus in the operative position the location and direction of a central axis of x-rays emitted from the first x-ray emitting apparatus is approximately identical to the location and direction of a central axis of x-rays emitted from the second x-ray emitting apparatus with the second x-ray emitting apparatus in the operative position.

8. The x-ray imaging apparatus according to claim 7, wherein the mounting is arranged on the support structure such that with the first x-ray emitting apparatus in the operative position the stand-off distance between it and the target has a first value, and with the second x-ray emitting apparatus in the operative position the stand-off distance between it and the target has a second value.

9. The x-ray imaging apparatus according to claim 8, wherein the first value is approximately 20 cm and the second value is approximately 10 cm.

10. The x-ray imaging apparatus according to claim 1, wherein the first and second x-ray emitting apparatus each comprise at least one collimator, the apparatus further comprising a mounting to which both the first and second x-ray emitting apparatus are attached such that an angle between longitudinal bores of the at least one collimator on each of the two x-ray emitting apparatus is approximately 180 degrees.

11. The x-ray imaging apparatus according to claim 1, further including at least one interlock which enables whichever of the first and second x-ray emitting apparatus is in the operative position to emit x-rays.

12. The x-ray imaging apparatus according to claim 1, including a sensor.

13. The x-ray imaging apparatus according to claim 12, wherein the sensor is an intra-oral sensor.

14. The x-ray imaging apparatus according to claim 12, wherein the sensor is a digital sensor.

15. The x-ray imaging apparatus according to claim 1, wherein the first x-ray emitting apparatus operates at a current in the range of 2.5 mA to 7 mA, and a voltage in the range of 60 to 70 kV.

16. The x-ray imaging apparatus according to claim 1, wherein the second x-ray emitting apparatus operates at a current in the range of 1 mA to 3 mA.

17. The x-ray imaging apparatus according to claim 1, further comprising a common power supply for both first and second x-ray emitting apparatus.

18. An x-ray imaging apparatus comprising a support structure, the support structure supporting two separate x-ray emitting apparatus, a first x-ray emitting apparatus comprising an x-ray emitter arranged for producing 2D images, and a second x-ray emitting apparatus comprising an array of distributed x-ray emitters arranged for producing 3D tomosynthesis images, the first and second x-ray emitting apparatus movable independently of one another relative to the support structure and arranged such that, in use, one of the first and second x-ray emitting apparatus is moveable into an operative position whereby x-rays are emitted therefrom towards a target, and simultaneously the other of the first and second x-ray emitting apparatus is movable into an inoperative position whereby x-rays are not emitted therefrom.

19. A method of obtaining 3D tomosynthesis x-ray images of a target, comprising the steps of: providing an x-ray imaging apparatus, the x-ray imaging apparatus comprising a support structure, the support structure supporting two separate x-ray emitting apparatus, a first x-ray emitting apparatus comprising an x-ray emitter arranged for producing 2D images, and a second x-ray emitting apparatus comprising an array of distributed x-ray emitters arranged for producing 3D tomosynthesis images, the first and second x-ray emitting apparatus moveable relative to the support structure and arranged such that, in use, one of the first and second x-ray emitting apparatus is moveable into an operative position whereby x-rays are emitted therefrom towards a target, and simultaneously the other of the first and second x-ray emitting apparatus is movable into an inoperative position whereby x-rays are not emitted therefrom; providing a target; arranging the first x-ray emitting apparatus in the operative position such that it is aimed at the target; operating the apparatus to provide a 2D x-ray image of the target; moving the first x-ray emitting apparatus into the inoperative position and moving the second x-ray emitting apparatus into the operative position such that it is aimed at the target; operating the apparatus to provide 3D tomosynthesis x-ray images of the target.

\* \* \* \* \*